US00PP21191P2

(12) United States Plant Patent
Laughner

(10) Patent No.: US PP21,191 P2
(45) Date of Patent: Aug. 10, 2010

(54) ***OSTEOSPERMUM* PLANT NAMED 'BALSERLEM'**

(50) Latin Name: *Osteospermum ecklonis*
Varietal Denomination: Balserlem

(75) Inventor: Linda Laughner, Ventura, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/460,610

(22) Filed: Jul. 22, 2009

(51) Int. Cl.
*A01H 5/00* (2006.01)

(52) U.S. Cl. ..... Plt./360

(58) Field of Classification Search ..... Plt./360
See application file for complete search history.

*Primary Examiner*—Annette H Para
*Assistant Examiner*—Louanne C Krawczewicz Myers
(74) *Attorney, Agent, or Firm*—Audrey Charles

(57) ABSTRACT

A new and distinct cultivar of *Osteospermum* plant named 'Balserlem', characterized by its medium yellow-colored flowers, medium green-colored foliage, and moderately vigorous, and upright-mounded growth habit, is disclosed.

1 Drawing Sheet

Latin name of genus and species of plant claimed: *Osteospermum ecklonis*.

Variety denomination: 'Balserlem'.

BACKGROUND OF THE INVENTION

The present invention relates to a new and distinct cultivar of *Osteospermum* plant botanically known as *Osteospermum ecklonis* and hereinafter referred to by the cultivar name 'Balserlem'.

The new cultivar originated in a controlled breeding program in Santa Paula, Calif. during June 2006. The objective of the breeding program was the development of *Osteospermum* cultivars that are freely flowering with unique flower coloration and a freely branching, compact, and upright growth habit.

The new *Osteospermum* cultivar was the result of a self-pollination of the proprietary *Osteospermum ecklonis* breeding selection designated 10925-1, not patented, characterized by its bright yellow-colored flowers, medium green-colored foliage, and moderately vigorous, upright growth habit. The new cultivar was discovered and selected as a single flowering plant within the progeny of the above stated self-pollination during February 2007 in a controlled environment at Santa Paula, Calif.

Asexual reproduction of the new cultivar by terminal stem cuttings since February 2007 at Santa Paula, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balserlem' as a new and distinct cultivar of *Osteospermum* plant:

1. Medium yellow-colored flowers;
2. Medium green-colored foliage; and
3. Moderately vigorous, and upright-mounded growth habit.

Plants of the new cultivar differ from plants of the parent primarily in flower color, flower size and growth habit. The new cultivar has a different shade of flower color, larger flowers, and a more mounded growth habit.

Of the many commercially available *Osteospermum* cultivars, the most similar in comparison to the new cultivar is TRADEWINDS Pure Yellow 'Oste Yel', U.S. Plant Pat. No. 19,050. However, in side by side comparisons, plants of the new cultivar differ from plants of 'Oste Yel' in at least the following characteristics:

1. Plants of the new cultivar have a ray floret color different from plants of 'Oste Yel';
2. Plants of the new cultivar have a smaller inflorescence diameter than plants of 'Oste Yel'; and
3. Plants of the new cultivar have a smaller disc diameter than plants of 'Oste Yel'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balserlem'. The plants were grown in 4.5 inch pots for 9 weeks in a greenhouse at West Chicago, Ill.

DETAILED BOTANICAL DESCRIPTION

Figure 1:
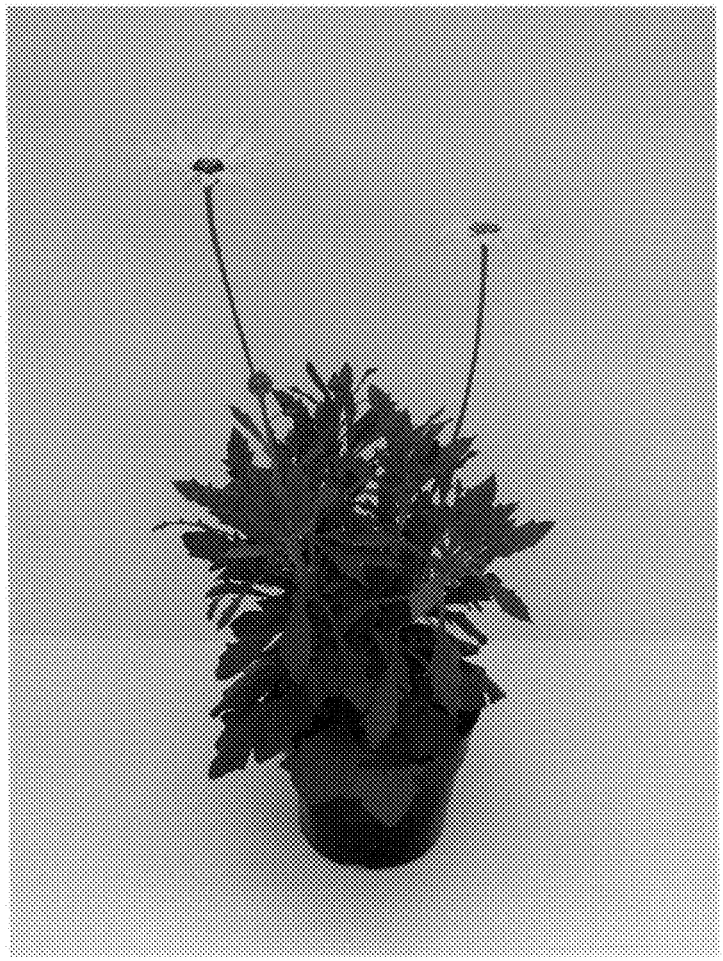
FIG. 1 illustrates a side view of the overall growth and flowering habit of 'Balserlem'.
Figure 2:
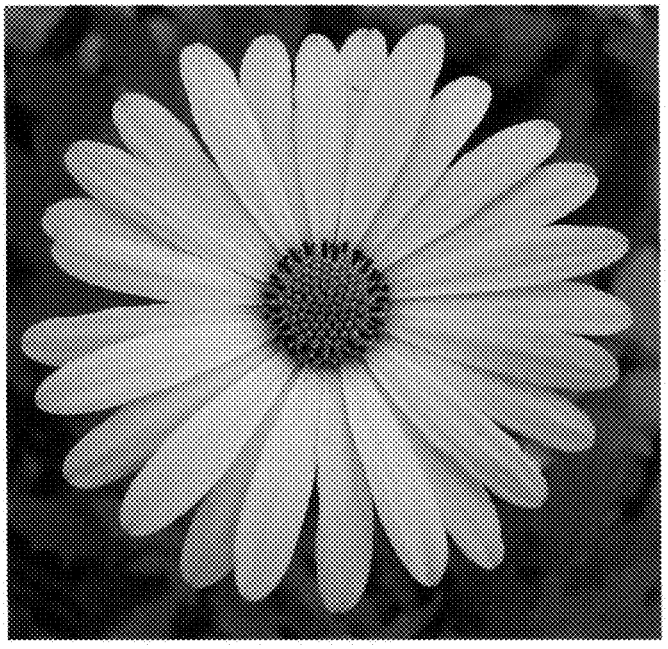
FIG. 2 illustrates a close-up view of an individual inflorescence of 'Balserlem'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in May 2009 under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 9 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Osteospermum ecklonis* cultivar Balserlem:

Parentage:

*Female and male parents.*—Proprietary *Osteospermum ecklonis* breeding selection designated 10925-1, not patented.

Propagation:

*Type cutting.*—Terminal stem.

*Time to initiate roots.*—Approximately 9 to 12 days.

*Time to produce a rooted cutting.*—Approximately 28 to 32 days.

*Root description.*—Fibrous.

*Rooting habit.*—Freely branching.

Plant description:

*Commercial crop time.*—Approximately 10 to 13 weeks from a rooted cutting to finish in a 10 cm pot.

*Growth habit and general appearance.*—Moderately vigorous and upright-mounded.

*Size.*—Height from soil level to top of plant plane: Approximately 28.4 cm. Width: Approximately 18.6 cm.

*Branching habit.*—Freely branching, pinching improves basal branching. Quantity of main branches per plant: Approximately 4.

*Branch.*—Strength: Strong. Length to base of peduncle: Approximately 6.0 cm. Diameter: Approximately 4.0 mm. Length of central internode: Approximately 4.5 mm. Texture: Glabrous. Color of young and mature stems: 144B.

Foliage description:

*General description.*—Quantity of leaves per main branch: Approximately 12. Fragrance: Pungent. Form: Simple. Arrangement: Alternate.

*Leaves.*—Aspect: Acute angle to stem becoming perpendicular to an obtuse angle with age. Shape: Spatulate. Margin: Widely dentate. Apex: Acute becoming rounded with age. Base: Attenuate. Venation pattern: Pinnate. Length of mature leaf: Approximately 5.1 cm. Width of mature leaf: Approximately 3.5 cm. Texture of upper surface: Sparsely pubescent. Texture of lower surface: Sparsely glandular pubescent. Gland color: Colorless. Color of upper surface of young foliage: 137A with venation of 145C. Color of lower surface of young foliage: 138B with venation of 144D. Color of upper surface of mature foliage: 137A with venation of 145B. Color of lower surface of mature foliage: 138A with venation of 144D.

*Petiole.*—Length: Approximately 2.6 cm. Diameter: Approximately 4.0 mm. Texture: Mixture of glandular and non-glandular pubescence. Gland color: Colorless. Color: 145B.

Flowering description:

*Flowering habit.*—'Balserlem' is freely flowering under outdoor growing conditions with substantially continuous blooming from spring through autumn and year-round in greenhouse environment.

*Lastingness of individual inflorescence on the plant.*—Approximately 8 to 10 days.

Inflorescence description:

*General description.*—Type: Solitary, composite. Persistent. Shape: Round. Aspect: Facing upward. Arrangement: Terminal, held above the foliage, arising from leaf axils. Disc and ray florets develop acropetally on a capitulum. Fragrance: Slight. Quantity per plant: Approximately 2. Diameter: Approximately 7.3 cm. Depth: Approximately 1.4 cm.

*Peduncle.*—Strength: Strong. Aspect: Erect. Length: Approximately 19.5 cm. Diameter: Approximately 2.0 mm. Texture: Glandular pubescent. Gland color: Colorless. Color: 144B.

*Bud.*—Rate of opening: Generally takes 4 to 6 days for bud to progress from first color to fully open flower. Quantity per plant: Approximately 2.

*Bud just before opening.*—Shape: Ovoid. Length: Approximately 1.5 cm. Diameter: Approximately 1.2 cm. Color: 154B.

*Ray florets.*—Quantity per inflorescence: Approximately 26. Arrangement: Imbricate in a single whorl. Aspect: Initially at acute angle to disc, becoming perpendicular at maturity. Shape: Oblanceolate. Margin: Entire. Apex: Emarginate with three tips. Base: Attenuate, fused to form a tube. Length: Approximately 3.5 cm. Width: Approximately 8.0 mm. Texture of upper surface: Glabrous. Texture of lower surface: Glabrous with a densely pubescent base. Color of upper surface when first open: Base of 4C transitioning toward apex to 5A. Color of lower surface when first open: Between 5B and 5C. Color of upper surface when fully open: Base of 4D transitioning toward apex to 5B. Color of lower surface when fully open: 5C.

*Disc florets.*—Quantity per inflorescence: Approximately 126. Arrangement: Massed in center of inflorescence. Shape: Tubular. Margin: Entire. Apex: Five acute tips. Base: Attenuate, fused. Length: Approximately 8.0 mm. Diameter at apex: Approximately 2.0 mm. Diameter at base: Approximately 1.0 mm. Texture: Glabrous with a sparsely pubescent outer surface. Color when fully open: Closest to 155D and base of 144D.

*Disc.*—Diameter: Approximately 1.4 cm. Depth: Approximately 5.0 mm.

*Receptacle.*—Shape: Conical. Height: Approximately 3.0 mm. Diameter: Approximately 4.0 mm. Color: 154D.

*Phyllaries.*—Quantity per inflorescence Approximately 26. Arrangement: In a single whorl. Shape: Linear to lanceolate. Margin: Entire. Apex: Acute. Base: Truncate. Length: Approximately 1.2 cm. Width: Approximately 2.0 mm. Texture of upper or inner surface: Densely pubescent at tip. Texture of lower or outer surface: Glandular pubescent. Gland color: Colorless. Color of upper or inner surface: 138B. Color of lower or outer surface: 138A.

*Reproductive organs.*—Androecium: Present on disc florets only. Stamen quantity: 5 per flower, fused around the style. Stamen length: Approximately 5.0 mm. Anther shape: Linear. Anther length: Approximately 2.0 mm. Anther color: N186A. Pollen amount: Abundant. Pollen color: 21A. Gynoecium: Present on ray and disc florets. Pistil quantity: 1 per floret. Pistil length: Approximately 8.0 mm. Stigma shape: Rounded. Stigma length: Less than 1 mm. Stigma color: N186A. Style length: Approximately 6.0 mm. Style color: Colorless, transparent. Ovary length: Approximately 2.0 mm. Ovary color: 144D.

Seed and fruit production: Neither seed nor fruit production has been observed.

Disease and pest resistance: Resistance to pathogens and pests common to Osteospermum has not been observed.

What is claimed is:

1. A new and distinct cultivar of *Osteospermum* plant named 'Balserlem', substantially as herein shown and described.

* * * * *